United States Patent
Gallem et al.

(12) 
(10) Patent No.: US 6,679,251 B1
(45) Date of Patent: *Jan. 20, 2004

(54) ACTUATING DEVICE FOR METERS AND METERING AEROSOL DISPENSING DEVICE WITH AN ACTUATING DEVICE FOR METERS

(75) Inventors: Thomas Gallem, Munich (DE); Kevin Stapleton, Boston, MA (US); Martin Knoch, Berg (DE)

(73) Assignee: Pari GmbH Spezialisten fur effektive inhalation, Starnberg (DE)

(*) Notice: Subject to any disclaimer, the term of this patent is extended or adjusted under 35 U.S.C. 154(b) by 0 days.

This patent is subject to a terminal disclaimer.

(21) Appl. No.: 09/807,104

(22) PCT Filed: Aug. 24, 1999

(86) PCT No.: PCT/EP99/06205
§ 371 (c)(1),
(2), (4) Date: Aug. 10, 2001

(87) PCT Pub. No.: WO00/21593
PCT Pub. Date: Apr. 20, 2000

(30) Foreign Application Priority Data

Oct. 8, 1998 (DE) ........................................ 198 46 382

(51) Int. Cl.7 ............................................. A61M 11/00
(52) U.S. Cl. ............................ 128/200.23; 128/205.23; 222/36
(58) Field of Search .................. 128/200.23, 206.27, 128/203.12, 205.26, 203.23, 205.23; 239/339, 71, 74; 222/41, 36, 38, 25, 28, 402.1–402.25; 116/308, 309

(56) References Cited

U.S. PATENT DOCUMENTS

| 5,349,945 A | 9/1994 | Wass et al. |
| 5,482,030 A | 1/1996 | Klein |
| 6,435,372 B1 * | 8/2002 | Blacker et al. ............... 222/23 |
| 6,481,438 B1 * | 11/2002 | Gallem et al. ......... 128/205.23 |

FOREIGN PATENT DOCUMENTS

| DE | 1 016 470 | 9/1957 |
| EP | 0 254 391 | 1/1988 |
| EP | 0 505 321 | 9/1992 |
| FR | 2 022 212 | 7/1970 |
| GB | 1 317 315 | 5/1973 |
| WO | WO86/02275 | 4/1986 |
| WO | WO93/24167 | 12/1993 |
| WO | WO95/34874 | 12/1995 |

* cited by examiner

Primary Examiner—Weilun Lo
Assistant Examiner—Mital Patel
(74) Attorney, Agent, or Firm—Merchant & Gould P.C.

(57) ABSTRACT

Metering aerosol dispensing device comprising an aerosol container (23); a nozzle (31, 32) that is arranged in a nozzle body (30), whereby the aerosol is dispensed via said nozzle when the aerosol container (23) is pushed against the body (30) of the nozzle once the metering aerosol dispensing device is actuated; a meter (1, 2, 4) that counts the number of times that the metering aerosol dispensing device is actuated; and an actuating device (10) that enables the meter (1, 2, 3, 4) to move forward when the metering aerosol dispensing device is actuated. The invention is characterized in that the actuating device (10) is designed and arranged in the metering aerosol dispensing device in such a way that the body (30) of the nozzle is accomodated in the interior of the actuating device (10) and the nozzle (31) is released in order to produce aerosol in an unrestricted manner.

8 Claims, 6 Drawing Sheets

ACTUATING DEVICE FOR METERS AND METERING AEROSOL DISPENSING DEVICE WITH AN ACTUATING DEVICE FOR METERS

The present invention refers to metering aerosol dispensing devices, and in particular to an actuating device for meters which can be easily used in metering aerosol dispensing devices.

There are known various metering aerosol dispensing devices for inhalation purposes which dispense an amount of medicament or drug of an exact dose in the form of a mist or an aerosol for instance for the treatment of respiratory tract diseases. Here, above all, the reliable metering of the dispensed medicament is important so that a specific therapeutical effect for the patient can be achieved. Such metering aerosol devices are for instance the generally known MDI (metered dose inhalers) which normally have a housing, a container for accommodating a liquid or powdery medicament, a suitably designed nozzle for atomizing and distributing the medicament, and a mouthpiece via which the generated medicament-containing aerosol is inhaled. In case of propellant aerosols, the actuation of the metering aerosol devices is effected for instance in such a way that the medicament container is displaced linearly with respect to the nozzle arranged in the housing, whereby a defined amount of the atomization material is released. A metering aerosol device of said kind is described for example in EP 0 254 391.

Metering aerosol dispensing devices usually are designed for multiple dosages. In this connection it is desirable that the number of the dispensed doses, in other words of the dispensed spraying puffs, or of the still available spraying puffs are indicated to the user in order to guarantee that the patient is informed at an early point of time of the fact that the medicament is consumed. Thereby it is avoided that a patient carries with him or her an already almost empty metering aerosol dispensing device for instance as a prophylaxis of an acute asthmatic attack.

Therefore controlled-dosage atomizers or controlled-dosage inhalers have been provided with different meters or counters. For instance in EP 0 254 391 there is described an inhaler with a flat meter which is formed on the side of an aerosol dispenser facing the patient. From EP 0 505 321 there is known a reusable inhaler with a resettable meter which is incremented when the first relative position of storage chamber and metering pin is reached. The meter disclosed in GB 1 317 315 has a plurality of annular elements which cooperate mechanically in order to indicate at an indicator ring the dosages still available. Further medicament dispensers with a mechanical meter are disclosed for instance in FR 2.022.212, WO 86/02275 and WO 93/24167.

The known solutions for metering devices, however, have either a complex, unmanageable structure or require rather considerable modifications of an already existing metering aerosol dispensing device. But such a modification of an already existing metering aerosol dispensing device is disadvantageous in that afterwards said device has once again to be subjected to an official approval procedure and the tests involved therewith regarding the medical applicability. This, however, usually is a tedious and expensive process and therefore is undesirable.

Consequently, proceeding from prior art, the object of the present invention is to develop for a metering aerosol device an actuating device for meters with small dimensions which can be used with different metering aerosol dispensing devices for counting the dosages without substantial modifications having to be carried out at the metering aerosol devices.

Said object is solved according to the invention by a metering aerosol dispensing device with an aerosol container, a nozzle arranged in a nozzle body, whereby an aerosol is dispensed via said nozzle when the aerosol container is displaced with respect to the nozzle body when the metering aerosol dispensing device is actuated, a meter for counting the actuations of the metering aerosol dispensing device, and an actuating device for shifting onward the meter when the metering aerosol dispensing device is actuated, wherein the actuating device comprises two sleeves displaceable, with respect to each other which, in the interior, accommodate the nozzle body of the metering aerosol dispensing device such that the nozzle is released in order to produce an aerosol in an unrestricted manner, wherein the sleeves are displaceable linearly with respect to each other and wherein the sleeves are connected with each other via spring elements which move the sleeves back into a starting position.

Advantageously, said spring elements are realized in the form of flat, curved spring elements which are fixed to the outsides of the sleeves or are integrally formed therewith.

In order to avoid a jamming of the sleeves, there are provided guiding elements at the sleeves of the actuating device which ensure a straight-lined displacement of both sleeves against each other. Alternatively, the spring elements can be designed such that they guarantee a linear displacement of both sleeves against each other.

For shifting or moving onward the meter, the actuating device comprises an actuating arm which acts upon the meter.

In order to realize as small a meter as possible, the meter consists of several disk units arranged in parallel, wherein a first disk unit has an external toothing which cooperates with the actuating device, in particular with the actuating arm.

In order to form a unit of the meter and the actuating device, the actuating device has an opening in which a bearing pin of the meter is fixed for holding the meter at the actuating device.

In order to ensure that the aerosol generation and spreading is not influenced, the actuating device, in particular the lower part thereof, is provided with a recess or an opening through which the nozzle is released.

Further features and advantages of the present invention result from the following description of a preferred embodiment which is described in connection with the accompanying drawings, wherein.

Figure 1:
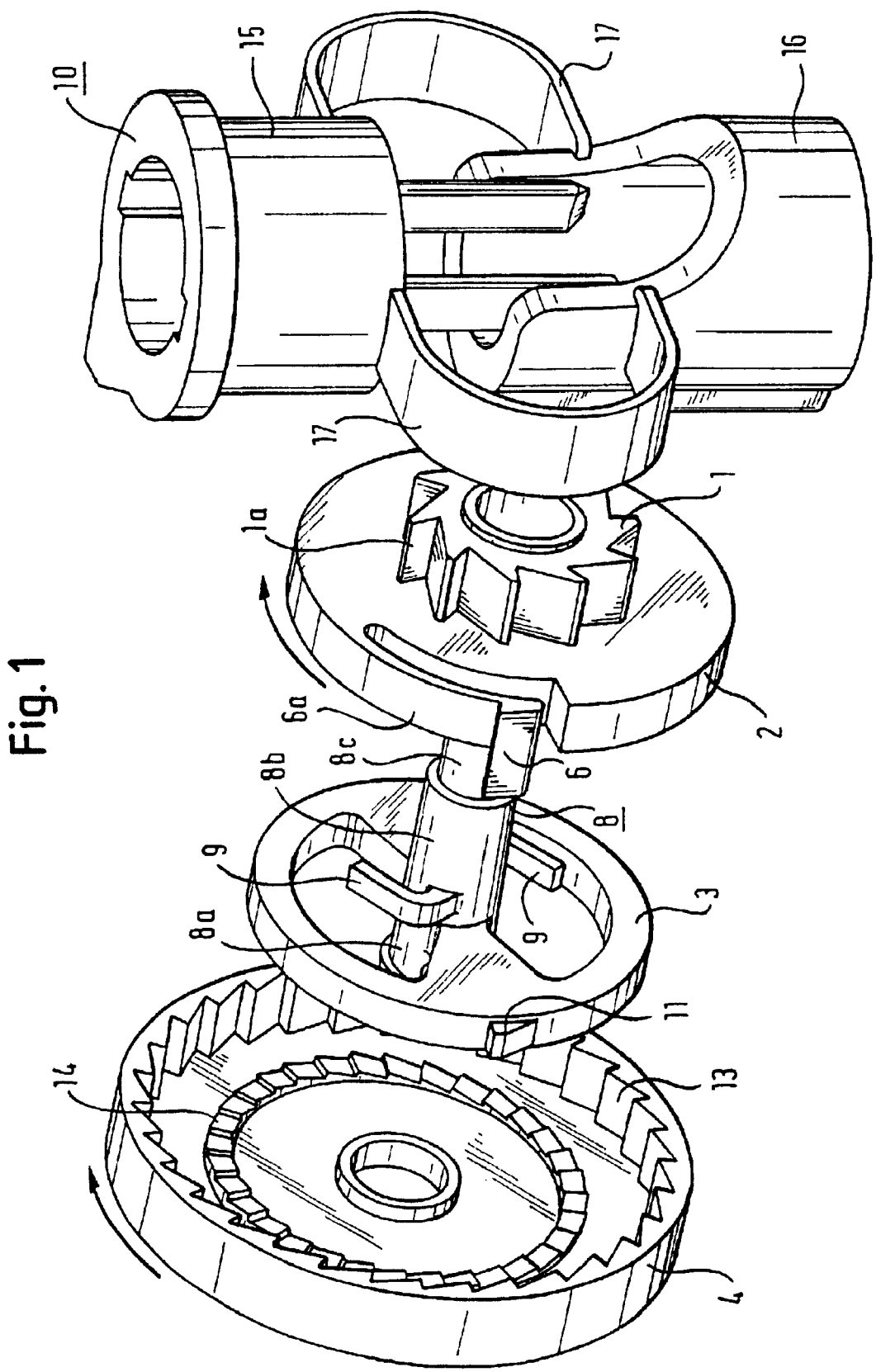
FIG. 1 shows an exploded view of a meter which cooperates with an inventive actuating device for a metering aerosol dispensing device.
Figure 2:
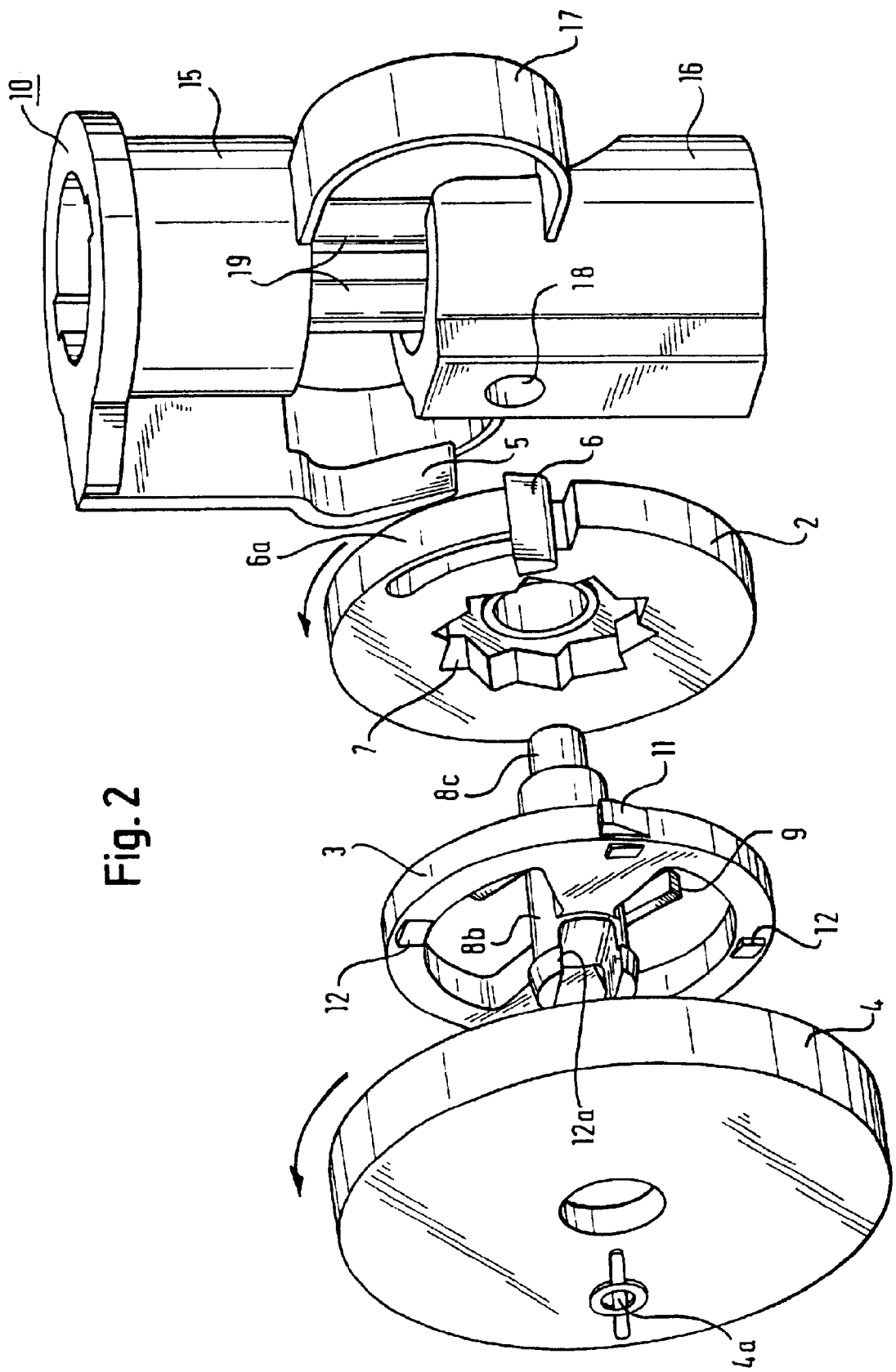
FIG. 2 shows an exploded view of the meter shown in FIG. 1, seen from a viewing direction different to that in FIG. 1.

As an introduction and for the sake of a better comprehension of the invention, in the following first of all a meter for metering aerosol dispensing devices is described with reference to FIGS. 1 and 2. FIGS. 1 and 2 each show exploded views of the meter viewed from two different viewing directions.

Essentially, the meter has four disk units 1, 2, 3 and 4 which are arranged in parallel to each other. The centers of the disk units 1, 2, 3 and 4 lie on an axis extending perpendiculary to the disk units and, as will be described in more detail in the following, are connected with an actuating device 10 of a metering aerosol generator (not shown) by means of a bearing pin 8. The first, second and fourth disk units 1, 2 and 4 are arranged rotatably relative to the actuating device 10. The third disk unit 3 has a fixed position relative to the actuating device 10 and thus also relative to the other disk units.

The first disk unit 1 has a means for receiving a force which effects a rotation of the first disk unit; said means is an external toothing 1a into which an actuating arm 5 attached at the actuating device 10 engages (see FIGS. 1 and 2). The first disk unit 1 has a smaller radius than the second disk unit 2 and is fixedly connected therewith. By said fixed connection the transmission of the rotation from the first disk unit 1 onto the second disk unit 2 is realized.

In order to transmit the motion of rotation to a fourth disk unit 4, as a transmission means a wedge-shaped cam 6 is arranged at the outer circumference of the second disk unit 2, said cam 6 being connected to the second disk unit 2 via a spring element 6a and being called a spring cam in the following. The spring element 6a forms substantially the outer contour of the second disk unit 2, but has a freely swinging end. At the freely swinging end the wedge-shaped spring cam 6 is arranged in such a way that in the rest position it projects over the outer contour of the second disk unit 2 in radial direction. The geometry of the spring cam is chosen such that the cam or nose engages the internal toothing 13 of the fourth disk unit 4 in case of a deviation in radial direction.

For this purpose, the wedge-shaped spring cam 6 is arranged such that the sharp and the blunt edge are orientated normal to the plane of the second disk unit 2. Furthermore, the spring cam 6 has a width which is larger than the thickness of the second disk unit 2 so that the spring cam 6 extends like a pin in parallel to the axis of the disk units in the direction towards the third and fourth disk unit 3 and 4.

In interaction with the other elements of the meter which will be explained in more detail particularly with reference to FIGS. 3 and 4, the spring cam 6 projecting like a pin in the direction of the third and fourth disk units can come into engagement with a first toothing 13 of the fourth disk unit 4 (see FIG. 2).

The side of the second disk unit 2 pointing towards the third and fourth disk unit has an internal toothing 7 which is arranged symmetrically around the axis of the disk units. The internal toothing 7, which is seen in FIG. 2 but not in FIG. 1, has the same number of teeth as the external toothing of disk unit 1. In the embodiment represented in FIG. 1 and FIG. 2, the number of teeth is ten so that together with a first internal toothing 13 of the fourth disk unit 4 with 24 teeth a total of 240 discrete steps of counting can be realized. But also other values can be easily used.

The radius of the third disk unit 3 is identical to or preferably slightly smaller than the radius of the second disk unit 2. Furthermore, at the outer circumference of the third disk unit 3 there is arranged a wedge-shaped shoulder 11 which is used for actuating the spring cam 6 arranged at the second disk unit 2 which will be explained in more detail in the following. When a further shoulder is arranged, the transmission ratio is changed. The third disk unit 3 is fixedly connected with a bearing pin 8.

With respect to the third disk unit 3, the bearing pin 8 has three different sections, namely section 8a pointing towards the fourth disk unit 4, and sections 8b and 8c pointing towards the first and second disk unit. The diameter of the bearing pin section 8b is identical to the diameter of section 8a, and the diameter of section 8c is reduced compared therewith. The bearing pin 8 is used for attaching the third disk unit 3 at the actuating device 10 such that the disk unit 3 is fixed with regard to a rotation therewith, and for the rotatable mounting of the first, second and fourth disk units 1, 2 and 4. For this purpose, the bearing pin section with the smaller radius 8c is inserted into a corresponding opening 18 of the actuating device 10 and secured such that the position of the third disk unit 3 relative to the actuating device 10 is fixed. The openings provided in the first and second disk units 1 and 2 are coordinated with the diameter of the bearing pin section 8b such that the first and second disk units 1 and 2 are slidably rotatable on the bearing pin section 8b. It is to be noted that the diameters of the sections 8a, 8b and 8c are not restricted to the ratio represented in FIG. 1 or FIG. 2. It is important that the respective openings of the disk units and the diameters of the bearing pin sections are coordinated with each other.

Furthermore, at the bearing pin 8 there are arranged two L-shaped locking elements 9 which are arranged at the outer circumference of the bearing pin section 8b and which engage into the internal toothing 7 of the second disk unit 2. The opening of the fourth disk unit 4 is coordinated with the diameter of the bearing pin section 8a in such a way that the fourth disk unit 4 is slidably rotatable on the bearing pin section 8a. At the section 8a there are also arranged symmetrically two snap hooks 12a pointing towards the fourth disk unit 4, said snap hooks 12a being used for the axial fixing of the disk unit 4.

On the side of the third disk unit 3 pointing towards the fourth disk unit 4 there is arranged a snap-in toothing 12 which can be seen in FIG. 2. In the embodiment represented in FIG. 2 the snap-in toothing 12 consists of four elements which are spaced apart from each other by 90°. The snap-in toothing can, however, also consist of one or of several elements which are arranged centrically around the axis of the bearing pin 8. Said snap-in toothing 12 comes into engagement with a second toothing 14 of the fourth disk unit 4 and is substantially used for securing the rotational position of the disk unit 4.

The design of the fourth disk unit 4 can be inferred in particular from FIG. 1. The side of the fourth disk unit 4 pointing towards the other disk units has a first toothing 13 which is arranged at the inside of the circumference, and a second toothing 14 circularly arranged around the central point of the fourth disk unit 4. The radius of the second toothing 14 is coordinated with the position of the elements of the snap-in toothing 12 provided at the third disk unit 3.

In the assembled state, the first and second disk units 1 and 2 are arranged on the bearing pin section 8b; here the L-shaped locking elements 9 rest in the recess of the internal toothing 7 of the second disk unit 2. The spring cam 6 projects over the outer contour of the third disk unit 3. The fourth disk unit 4 is arranged on the bearing pin section 8a and, due to its cap-like form, accommodates the third disk unit 3; here the spring cam 6 lies between the outer contour of the third disk unit 3 and the first internal toothing of the fourth disk unit 4.

In the following the functioning of the above described meter is explained. Since the actuating arm 5 of the inventive actuating device 10 engages into the external toothing of the first disk unit 1, as is shown in FIG. 2, by a movement of the actuating arm 5 the first disk unit 1 is rotated in the direction of the arrow indicated in FIGS. 1 and 2. In this connection the second disk unit 2 is rotated therewith, as the first and second disk units 1 and 2 are fixedly connected with each other. Here the first and second disk units 1 and 2 slide along the bearing pin section 8b. In contrast thereto, the third disk unit 3 is fixedly connected to the actuating device 10 via the bearing pin 8 so that the position of the third disk unit 3 relative to the actuating device 10 remains unchanged at any time. Simultaneously, the L-shaped locking elements 9 arranged at the bearing pin section 8b are in engagement with the internal toothing 7 of the disk unit 2; but the design of the locking elements 9 and of the internal toothing 7 allows a rotation of the first and second disk units 1 and 2 in the direction shown in FIGS. 1 and 2. When the first and second disk units 1 and 2 are rotated in the direction of the arrow, the locking elements 9 lock into the respective following toothing of the internal toothing 7. When the arm 5 is operated once again, the disk units 1 and 2 rotate on by exactly one tooth and the locking arm engages the next tooth. By such an engagement of the locking elements 9 into the internal toothing 7 it is guaranteed that the first disk unit and thus also the second disk unit do not rotate backwards when the actuating arm 5 is released out of engagement with the disk unit 1 which is shaped like a toothed wheel, i.e. that they do not move backwards contrary to the direction of the arrow.

When the first and second disk unit 1 and 2 are rotated in the direction of the arrow as indicated in FIGS. 1 and 2, the spring cam 6 arranged at the second disk unit 2 runs along the outer contour of the third disk unit 3. When proceeding from a toothed gear with ten teeth and when the arm 5 is actuated ten times, the spring cam 6 moves over an angle of 360°, i.e. the spring cam makes one complete rotation and reaches again its starting position. As long as the spring cam 6 is not influenced by the shoulder 11 of the third disk unit 3, the spring cam 6 does not engage into the first toothing 13 arranged at the inner circumferential side of the fourth disk unit 4. Only when the shoulder 11 raises the spring cam 6 in radial direction, the spring cam 6 comes into engagement with the first internal toothing of the fourth disk unit 4 and effects a rotation of the fourth disk unit around a rotational position.

The step-by-step rotation of the disk unit 2 relative to the third disk unit 3 as well as the engagement of the spring cam 6 of the second disk unit 2 into the internal toothing 13 of the fourth disk unit 4 are described in detail in the following with reference to FIGS. 3 and 4. FIGS. 3 and 4 show schematical cross-sectional views which explain in particular the cooperation of the second and third disk units 2 and 3 in a more detailed manner. In FIGS. 3 and 4 the disk units 2 and 3 are represented viewed from the direction of view shown in FIG. 2. For reasons of a better general survey, the third disk unit 3 is indicated in both representations only in broken lines. FIG. 3 shows the above-mentioned starting position or resting position of the second disk unit 2 relative to the third disk unit 3 fixedly connected with the actuating device 10. In said position the locking element 9 is locked in the first tooth 7-1 of the internal toothing 7. By actuation of the actuating arm 5 which engages into the toothed wheel-shaped first disk unit 1 (not shown in FIG. 3), the disk unit 2 is rotated step-by step, i.e. tooth by tooth, in the direction of the arrow as indicated in FIG. 3. Here, starting from the first inner tooth 7-1, the locking element 9 engages the teeth 7-2 through 7-9 in ascending order. During the rotation of the first and second disk unit 1 and 2 initiated by the actuating arm 5, the spring cam 6 runs along the circumference of the third disk unit 3 represented by a broken line in FIG. 3 without any deviation of the spring cam 6. In this case the spring cam 6 does not engage into the first toothing 13 of the fourth disk unit 4.

Figure 3:
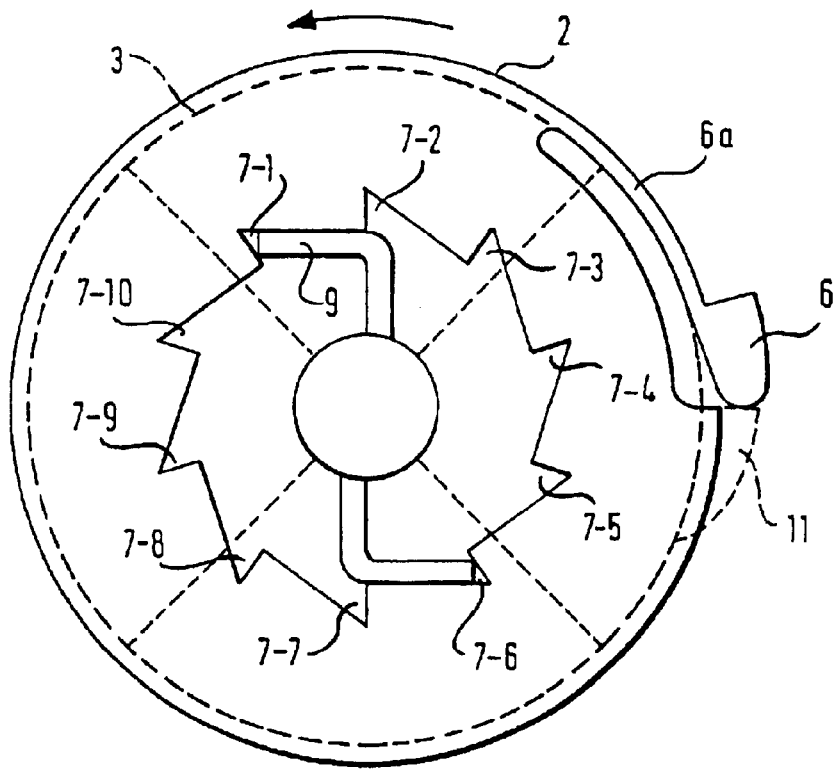
FIG. 3 shows a schematic cross-sectional view of a starting position or resting position of the second and third disk units for explaining the cooperation between the second and third disk units.
Figure 4:
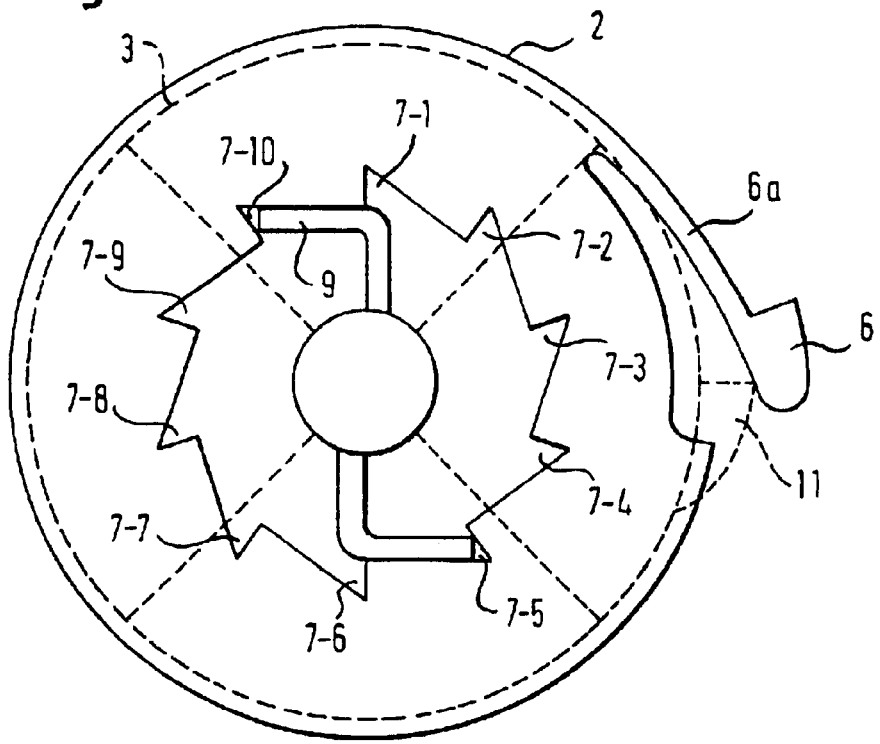
FIG. 4 shows a schematic cross-sectional view analogous to FIG. 3 which illustrates the second and third disk units in a position in which the second disk unit is caused by the third disk unit to cooperate with the fourth disk unit.

When the actuating arm 5 has been actuated so often that the locking element 9 locks into the tooth 7-10 of the internal toothing 7, i.e. when, proceeding from the starting position shown in FIG. 3, the actuating arm 5 has been actuated for the ninth time, then the spring cam 6 is in contact with the shoulder 11. The effect thereof is that the spring cam 6, as is shown in FIG. 4, is deviated in radial direction. In other words, the spring cam 6 is actuated in this position by the shoulder 11 and the spring cam 6 engages the toothing 13 at the inner circumference and rotates the fourth disk unit 4 forward by one tooth of the first toothing 13 in the direction of the arrow.

During this rotation of the fourth disk unit 4 effected by the cooperation of the shoulder 11 and the spring cam 6, the second toothing 14 arranged at the inside of the fourth disk unit 4 pointing towards the first, the second and the third disk unit comes into engagement with the snap-in toothing 12. The snap-in toothing 12 and the second toothing 14 of the fourth disk unit 4 here serve to secure the fourth disk unit 4 against rotation, and by the snap hooks 12a there is guaranteed an axial fixation of the fourth disk unit 4.

In the following actuation of the first or second disk unit by the actuating arm 5, the second disk unit 2 once again resumes the starting position represented in FIG. 3, and the movement of the spring cam 6 described above with reference to FIG. 3 is once again passed through, without the spring cam 6 coming into engagement with the first toothing 13 of the fourth disk unit 4. Only when the locking element once again locks into the tooth 7-10 of the internal toothing 7, the spring cam 6 is once again deviated by the shoulder 11 so that it comes again into engagement with the internal toothing 13 and thereupon rotates the fourth disk unit 4 forward by one tooth of the first internal toothing 13. In this way, when the first disk unit has ten teeth, the fourth disk unit 4 is rotated further by exactly one tooth of the first toothing 13 each time after ten actuations of the actuating arm 5. When the first internal toothing 13 of the fourth disk unit 4 has for instance 24 teeth, the maximum number of counting positions in this case amounts to 240, i.e. when the fourth disk unit 4 is rotated by 360°, 240 actuations of the actuating arm 5 are counted. The second toothing 14 of the fourth disk unit 4 has the same number of teeth as the first internal toothing 13.

It is to be noted that the number of teeth of the first and second toothings 13 and 14 can be adapted correspondingly to the desired transmission. A 30-teeth first or second toothing 13 or 14 thus can be used for a counting of up to 300 actuations. The transmission ratio of the inventive meter or the number of countings, however, can also be varied by arranging another shoulder or several shoulders at the outer edge of the third disk unit 3. This enables in particular an uncomplicated and rapid adaptation of the inventive meter to a desired transmission ratio.

The fourth disk unit 4 can be designed in the form of an indicating disk in order to indicate the countings correspondingly. This can be achieved for instance by an imprinted pointer or a color marking on the front side as well as on the edge of the fourth disk unit 4. In the embodiment represented in FIG. 2 there is indicated a pointer indicating element 4a. In accordance with the rotational position of the fourth disk unit 4, the pointer indicates the number of actuations.

In the following the actuating device 10 according to the invention which in an advantageous manner cooperates with the above described meter, but, if necessary, also with other meters, is explained as an example in detail.

Figure 5:
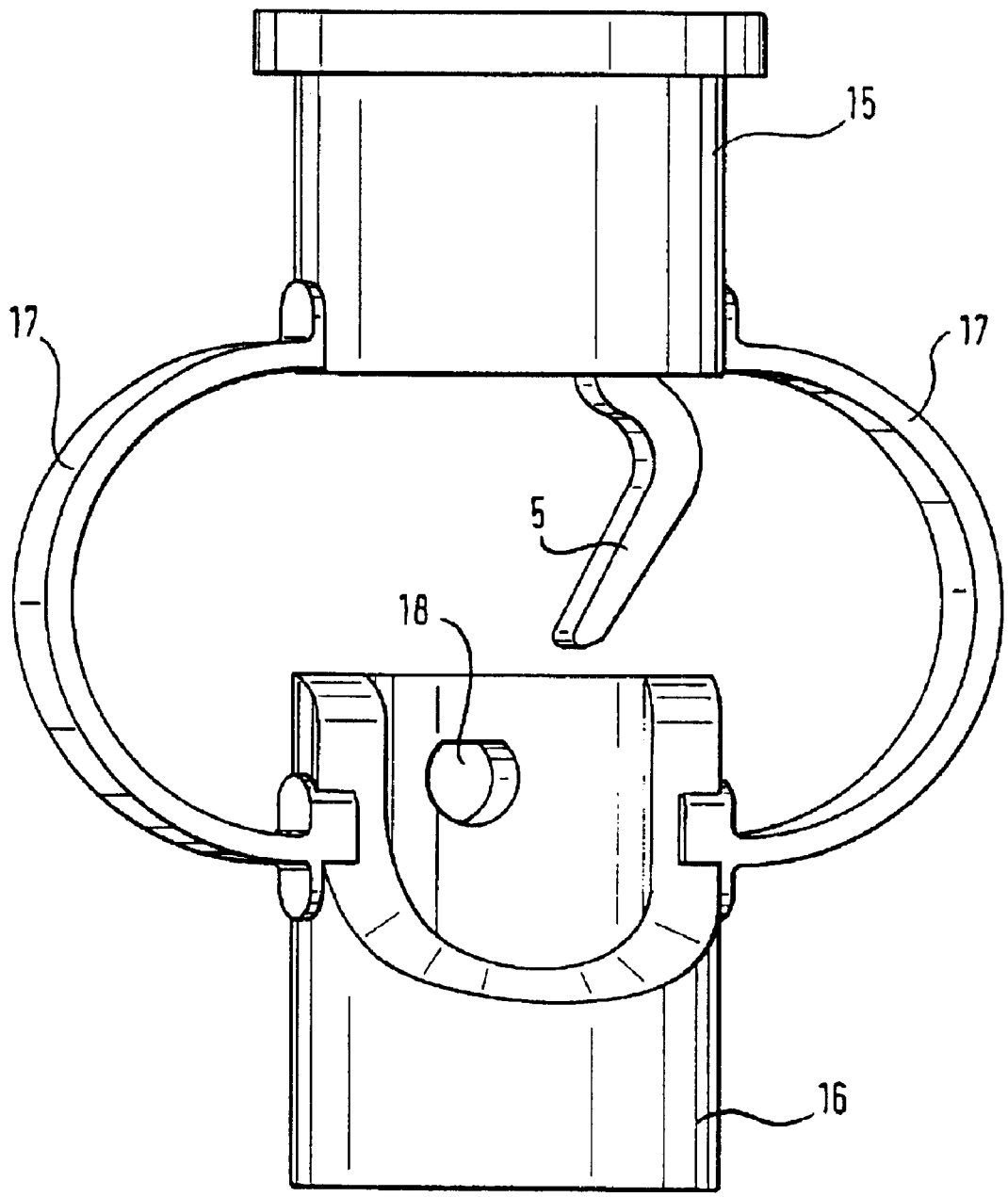
FIG. 5 shows a separate view of the actuating device represented in FIGS. 1 and 2.

The actuating device 10 represented in FIGS. 1 and 2 includes a cylindrical sleeve 15 and a cylindrical lower part 16 which is also a sleeve. At the outside of sleeve 15 there is arranged an actuating arm 5. The sleeve 15 and the lower part 16 are connected to each other via an arcuate spring 17. When the spring 17 is actuated, i.e. when the sleeve 15 and the lower part 16 are pressed together in axial direction, a linear movement of the sleeve 15 relative to the lower part 16 is guaranteed by suitable guiding elements 19 which are arranged at the sleeve 15 in a manner pointing towards the lower part 16. Therein the inner circumferential side of the sleeve 15 slides along the outside of the guiding elements 19. It is essential that a straight-lined movement of the sleeve 15 and thus also a straight-lined movement of the actuating arm 5 are guaranteed when the actuating device 10 is pressed together, and a reliable engagement of the actuating arm 5 into the toothed wheel-shaped first disk unit 1 is obtained. Due to the design of the curved spring 17 as a flat curved spring element, as is for instance shown in FIGS. 1 and 2, a linear movement of the sleeve 15 relative to the lower part can be obtained without guiding elements being required. For an illustration thereof there is represented a corresponding design of the actuating device 10 in FIG. 5, wherein the meter was omitted in the representation of FIG. 5.

Figure 6:
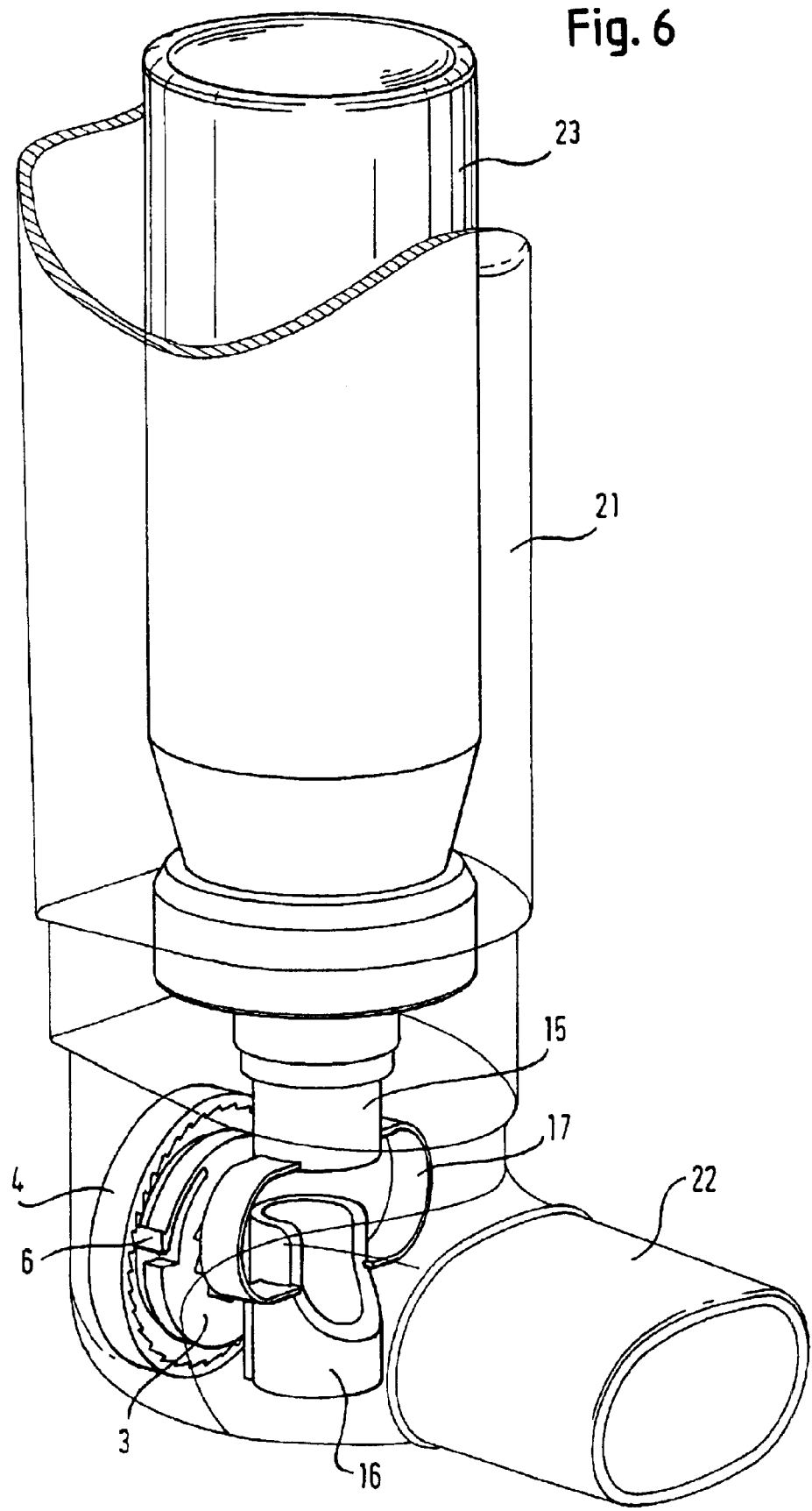
FIG. 6 shows the arrangement of the inventive actuating device for meters in a metering aerosol dispensing device.

FIG. 6 shows a total view of the arrangement of the inventive actuating device and of the above described meter in a metering aerosol dispensing device. FIG. 6 shows a housing 21 of the metering aerosol dispensing device which is provided with a mouthpiece 22. The mouthpiece 22 is arranged at the lower section of the housing 21 in an angular position. In the upper section of the housing 21 there is a metering aerosol container 23 for receiving an aerosol to be atomized. At the lower section of the aerosol container 23 there follows a nozzle section which is inserted into the guiding sleeve 15 of the actuating device 10. For the illustration of the position of the inventive actuating device, the nozzle itself is not shown in FIG. 6. The actuating device 10 is connected with the inventive meter consisting of disk units 1, 2, 3 and 4 in order to count and indicate the dispensed or still remaining dosages. During each pumping puff which, as described above, is triggered by the actuation of the metering aerosol dispensing device, a certain amount of aerosol is dispensed and atomized via a nozzle the structure and use of which in such conventional metering aerosol dispensing devices is generally known. The generated aerosol can be inhaled by a patient via the mouthpiece 22. The actuation of the metering aerosol device effects that the guiding sleeve 15 together with the actuating arm of the actuating device 10 is displaced with respect to the lower part 16. Thereby the actuation of the metering aerosol dispensing device results in a shifting onward of the meter.

Figure 7:
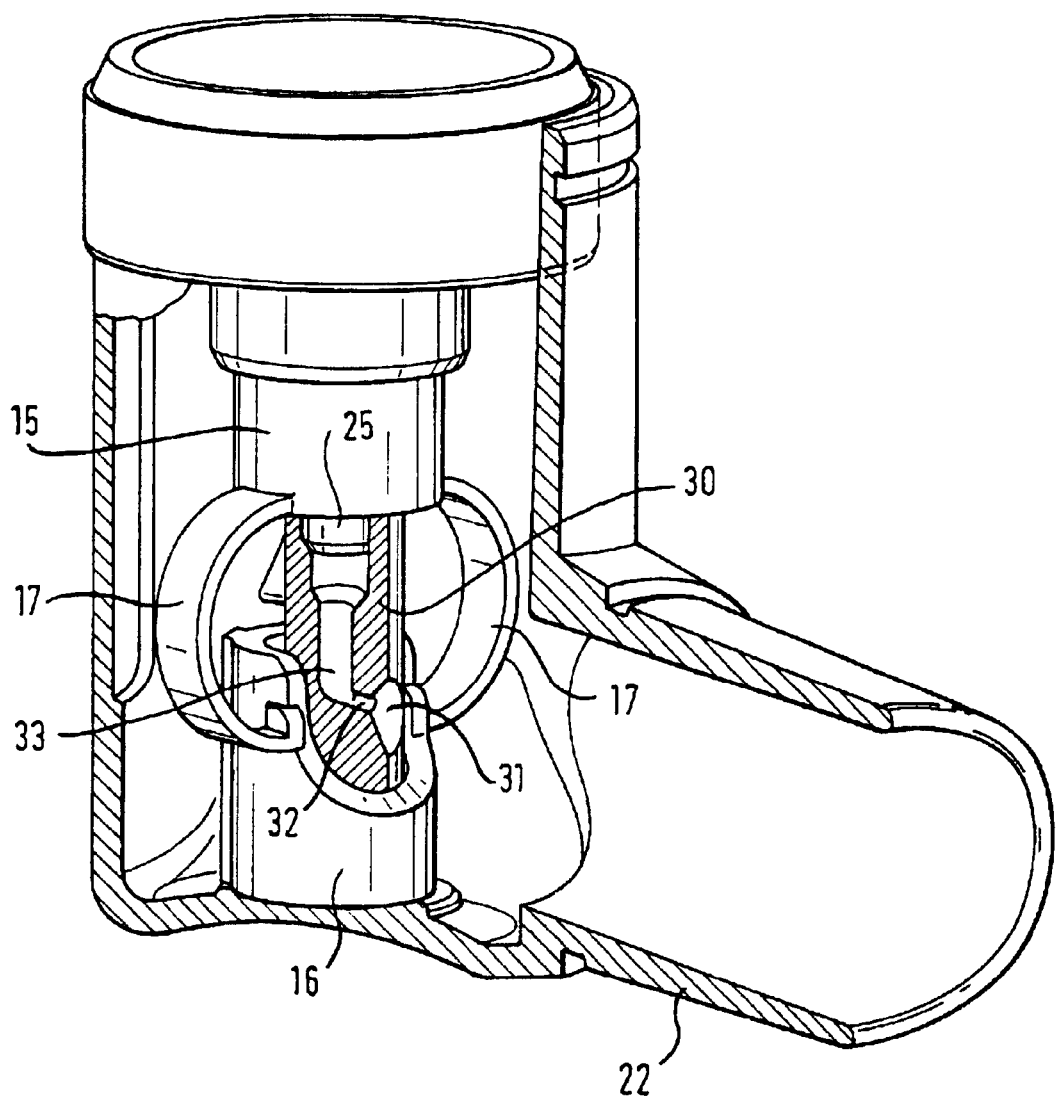
FIG. 7 shows an enlarged representation of the arrangement of the actuating device at the nozzle of a metering aerosol dispensing device.

As can be learnt from FIG. 6, the meter together with the inventive actuating device can be arranged readily below the aerosol container in a conventional metering aerosol dispensing device. This is above all achieved by the fact that, as already to be inferred from FIG. 6, the sleeve 15 as well as the lower part 16 of the actuating device 10 have room in the inside for in particular the connecting piece (not visible) of the aerosol container 23 and for the nozzle body of the metering aerosol dispensing device. In FIG. 7 it is shown how a cylindrical nozzle body 30 of the metering aerosol dispensing device 21 can be arranged in the sleeve 15 and the lower part 16 of the actuating device 10. Here there are shown the cylindrical nozzle body 30 (represented in section), the funnel-shaped nozzle opening 31, a connecting channel 32 which connects the funnel-shaped nozzle opening 31 with a nozzle chamber 33 into which the connecting piece 25 of the aerosol container 23 discharges the aerosol in case of a pumping puff. As, according to the invention, the sleeve 15 and the lower part 16 of the actuating device 10 in the inside thereof offer sufficient space for the nozzle 30 as well as also for the connecting piece of the aerosol container 23, and as the lower part 16 is designed such that it releases the nozzle 31 completely and does not influence the aerosol production and spreading, the actuating device 10 can be easily arranged at the nozzle body of a given metering aerosol dispensing device without changes having to be carried out at the nozzle body 30 or at the nozzle 31, 32 or at the connector 25 for the aerosol container. This means that the metering aerosol dispensing device has not to be subjected to a new approval procedure, as because of the actuating device 10 according to the invention no modifications have to be carried out at the nozzle design 30, 31, 32, 33.

In the shown example of an inventive actuating device, the release of nozzle 31 is achieved in that the sleeve forming the lower part 16 has a corresponding recess on the side facing the nozzle, as is shown in FIGS. 1, 2, 5, 6, and 7. Alternatively, also an opening can be provided which is similar to the opening 8, but which is designed such that it releases the nozzle 31.

Thus it is advantageous that a conventional metering aerosol dispensing device has not to be changed in its essential components, in particular not the nozzle, when a meter is used with an actuating device 10 according to the invention. By a simple arrangement of an actuating device for actuating the meter in a given device design, an easier and simpler structure is rendered possible which can be used universally with already known devices. Thereby an expensive modification of the already known metering aerosol dispensing devices can be dispensed with. This is of particular advantage, as for instance in case of a change of the nozzle form such inhalers have to be subjected once again to medical tests for obtaining an approval, which normally are tedious, sumptuous and thus also costly.

What is claimed is:

1. Metering aerosol dispensing device with an aerosol container (23), a nozzle (31, 32) arranged in a nozzle body (30), wherein an aerosol is dispensed via said nozzle when the aerosol container (23) is displaced with respect to the nozzle body (30) once the metering aerosol dispensing device is actuated, a meter (1, 2, 3, 4) for counting the actuations of the metering aerosol dispensing device, and an actuating device (10) for shifting onward the meter (1, 2, 3, 4) when the metering aerosol dispensing device is actuated, characterized in that the actuating device (10) includes two sleeves (15, 16) which are displaceable with respect to each other, which, in the inside thereof, accommodate the nozzle body (30) of the metering aerosol dispensing device such that the nozzle (31) is released for an aerosol production without any restrictions, which are displaceable linearly with respect to each other, and which are connected to each other by means of spring elements (17) which move the sleeves (15, 16) back into a starting position.

2. Metering aerosol dispensing device according to claim 1, characterized in that the spring elements (17) are realized in the form of flat, curved spring elements which are secured at the outsides of the sleeves (15, 16) or are integrally formed therewith.

3. Metering aerosol dispensing device according to claim 1, characterized in that at the sleeves (15, 16) of the actuating device (10) guiding elements (19) are provided which guarantee a linear displacement of the two sleeves (15, 16) with respect to each other.

4. Metering aerosol dispensing device according to claim 1, characterized in that the spring elements (17) are designed such that they guarantee a linear displacement of the two sleeves (15, 16) with respect to each other.

5. Metering aerosol dispensing device according to claim 1, characterized in that the actuating device (10) has an actuating arm (5) which acts upon the meter in order to shift onward the meter.

6. Metering aerosol dispensing device according to claim 1, characterized in that the meter is constructed of several disk units (1, 2, 3, 4) arranged in parallel and that a first disk unit has an outer toothing (1a) which cooperates with the actuating device (10).

7. Metering aerosol dispensing device according to claim 1, characterized in that the actuating device (10) has an opening (18) in which a bearing pin (8c) of the meter is fixed for holding the meter at the actuating device (10).

8. Metering aerosol dispensing device according to claim 1, characterized in that the actuating device (10) has a recess or an opening through which the nozzle (31) is released.

* * * * *